United States Patent [19]

Chen et al.

[11] Patent Number: 5,030,768

[45] Date of Patent: Jul. 9, 1991

[54] PROCESS FOR PREPARING ALKYL TERT-ALKYL ETHERS

[75] Inventors: Michael S. Chen, Zionsville; Shivaji Sircar, Wescosville, both of Pa.

[73] Assignee: Air Products and Chemicals, Inc., Allentown, Pa.

[21] Appl. No.: 502,585

[22] Filed: Mar. 30, 1990

[51] Int. Cl.$^5$ .............................................. C07C 41/06
[52] U.S. Cl. ..................................... 568/697; 568/699
[58] Field of Search ................................ 568/697, 699

[56] References Cited

U.S. PATENT DOCUMENTS

| | | | |
|---|---|---|---|
| 3,726,942 | 4/1973 | Louder | 260/683.61 |
| 4,409,421 | 10/1983 | Herwig et al. | 585/833 |
| 4,447,653 | 5/1984 | Vora | 568/697 |
| 4,605,787 | 8/1986 | Chu et al. | 568/697 |
| 4,774,365 | 9/1988 | Chen et al. | 568/697 |

FOREIGN PATENT DOCUMENTS

205562 6/1986 European Pat. Off. .

*Primary Examiner*—Howard T. Mars

*Attorney, Agent, or Firm*—Keith D. Gourley; James C. Simmons; William F. Marsh

[57] ABSTRACT

A process for preparing an alkyl-tert-alkyl ether wherein an olefin having a double bond on a tertiary carbon atom and a primary alcohol are reacted in the presence of a catalyst under conditions sufficient to produce an azeotropic alcohol/ether/hydrocarbon mixture containing the alkyl-tert-alkyl ether. The azeotropic alcohol/ether/hydrocarbon mixture is subjected to a cyclic liquid phase adsorption process sequence to selectively remove the alcohol. The resulting non-azeotropic ether/hydrocarbon stream can then be easily separated by distillation to provide the desired alkyl-tert-alkyl ether product and a hydrocarbon product. The cyclic adsorption process employed to separate the alcohol from the ether/hydrocarbon mixture comprises introducing the alcohol/ether/hydrocarbon mixture into a plurality of adsorption colums containing an alcohol selective adsorbent, wherein each respective absorption column undergoes successive steps of adsorption and desorption.

11 Claims, 1 Drawing Sheet

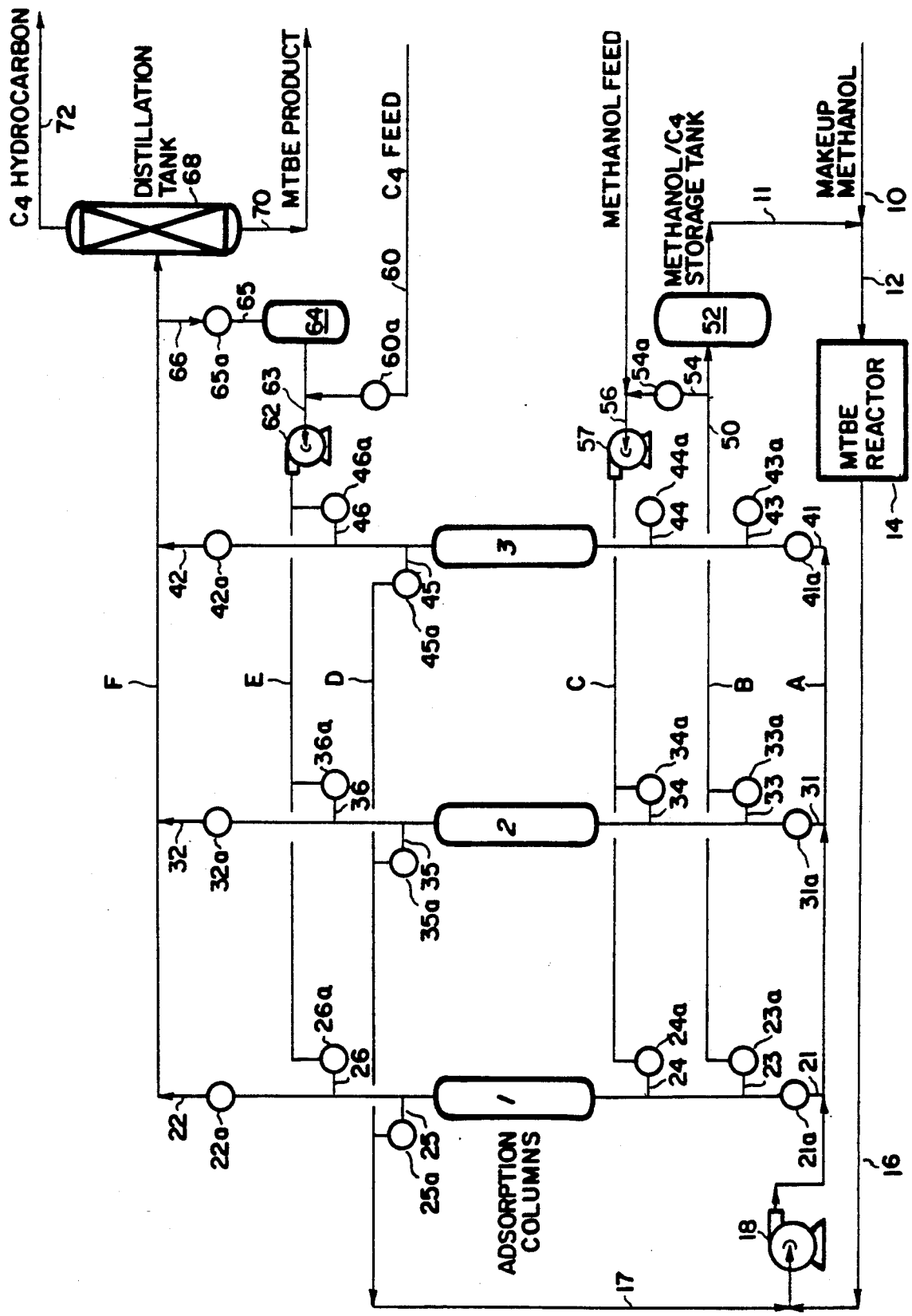

PROCESS FOR PREPARING ALKYL TERT-ALKYL ETHERS

TECHNICAL FIELD

The present invention relates to a process for preparing alkyl-tert-alkyl ethers wherein a primary alcohol and an olefin having a double bond on a tertiary carbon atom are reacted in the presence of a catalyst to form an azeotropic alcohol/ether/hydrocarbon product mixture. The product mixture is separated by employing a cyclic concentration swing adsorption sequence to selectively remove the alcohol followed by distillation of the non-azeotropic ether/hydrocarbon stream to separate the process stream into the respective ether and hydrocarbon products.

BACKGROUND OF THE INVENTION

Processes for producing alkyl tert-alkyl ethers by reacting a primary alcohol with a tertiary olefin having from 4 to 7 carbon atoms over a suitable catalyst are well known in the art. Two representative ethers which have considerable commercial success as motor fuel octane enhancers are methyl tert-butyl ether (MTBE) and tert-amyl methyl ether (TAME) which are made by reacting isobutylene and isopentenes, respectively, with methanol.

Etherification reactions are exothermic and equilibrium-limited and are generally carried out in the liquid phase in catalytic reactors having one or two fixed beds wherein heat is removed by circulating liquid through external heat exchangers. Etherification catalysts are generally strongly acidic ion exchange resins.

Tertiary olefin conversions obtained in conventional etherification reactions employing a single reactor wherein excess methanol is utilized, are generally limited to within the range of 90 to 96%. To achieve higher conversion, a two-stage reactor system using between 2 and about 20% excess methanol is generally practiced. The use of excess alcohol also suppresses polymerization of olefins to dimers and trimers. Unfortunately, methanol forms azeotropic mixtures with ethers and $C_4$ to $C_7$ hydrocarbons wherein separation by ordinary distillation is very difficult and, as a result, both energy- and capital-intensive.

Several techniques have been disclosed in the prior art for removing methanol from azeotropic etherification products. For example, U.S. Pat. No. 3,726,942 discloses a MTBE process in which the MTBE effluent stream is first sent to a distillation column to separate MTBE (bottom product) from the $C_4$ hydrocarbon (overhead product). The crude MTBE product is water washed to remove methanol. The crude $C_4$ hydrocarbon product is also water washed to remove methanol; alternatively, mol sieve is used to remove methanol. The methanol-water mixture is then separated by distillation and the methanol fraction is recycled to the MTBE reactor.

Patent Application EP-205562 discloses a process for preparing methyl-tert-alkyl ether which comprises: (a) contacting and reacting in the liquid phase a reaction mixture formed by combining a stream consisting essentially of $C_4$-$C_5$ hydrocarbons and containing at least some proportion of isoalkylene and a stoichiometric excess of methanol, with respect to the isoalkylene, to form a reaction product comprising methyl-tert-alkyl ether, unreacted methanol and unreacted $C_4$-$C_5$ hydrocarbons; (b) isolating the methyl-tert-alkyl ether from the reaction product and (c) recovering the unreacted methanol from the residual portion of the reaction product; the improvement which comprises selectively adsorbing the methanol constituent of said residual reaction product in a bed of crystalline molecular sieve adsorbent and recovering the same by desorption using the $C_4$-$C_5$ hydrocarbon, used to prepare the initial reaction mixture, as a purge-desorption stream.

French Patent 2,448,521-A discloses a process for producing ethers which comprises (a) reacting an alcohol with a tertiary olefin in the presence of an acid catalyst to produce an effluent containing ether, unreacted alcohol and unreacted hydrocarbons; (b) contacting the effluent with a molecular sieve capable of adsorbing the alcohol but not the ether; (c) distilling the non-adsorbed product to separate the ether from the hydrocarbons; (d) periodically interrupting step (b) and contacting the alcohol-laden molecular sieve with a stripping gas at a temperature sufficient to desorb the alcohol; and (e) adjusting the temperature and pressure of the effluent gas from step (d) to condense the alcohol. The process is stated to be especially useful for producing methyl tert-butyl ether.

U.S. Pat. No. 4,409,421 discloses a process for preparing a pure tertiary olefin in which an alkanol and an alkyl-tert-alkyl ether are separated by distillation followed by adsorption using synthetic ion exchange resins. U.S. Pat. No. 4,447,653 discloses a process for regenerating adsorbents used in an integrated process for producing ethers such as methyl tert-butyl ether. The regeneration procedure includes contacting the adsorbent with a portion of the treated hydrocarbon stream. The resultant contaminated hydrocarbon stream is passed into a stripping column used to remove the lights from the effluent of a dehydrogenation zone in which the isoolefin fed to the etherification zone is produced. The hydrocarbonaceous compounds collected on the adsorbent are thus recycled rather than being destroyed or lost in low purity effluent streams. The contaminated hydrocarbon stream may also be passed directly into the etherification zone.

U.S. Pat. No. 4,605,787 discloses a process for preparing MTBE which comprises reacting in vapor phase at a temperature between 170° and 220° F., methanol with isobutylene in the presence of ZSM-5 or ZSM-11 acidic zeolite catalyst characterized by having a constraint index of from about 1 to 12 and a silica/alumina ratio of at least 5. Removal of any excess methanol is accomplished by passing the reaction product through a bed of small pore zeolite.

U.S. Pat. No. 4,774,365 discloses an improved process for separating alcohols from ethers and/or hydrocarbon mixture in an etherification process. The excess alcohol reactant, which forms azeotropic mixture with the product ether and unreacted $C_4$-$C_7$ hydrocarbons, is removed by passing the liquid azeotropic mixture over a pervaporation membrane which effectively breaks the azeotrope and permeates the alcohol with high flux and high selectivity.

A need exists in the art for an energy efficient, less capital intensive process for making alkyl tert-alkyl ethers, and more particularly, to an energy efficient cyclic process for removing unreacted alcohol from the azeotropic etherification reaction product mixture.

BRIEF SUMMARY OF THE INVENTION

The present invention provides an energy efficient, cyclic process for effectively breaking the alcohol/ether/hydrocarbon azeotrope formed during the production of ethers wherein a novel cyclic adsorption sequence is employed to remove the alcohol from the azeotropic mixture such that the resulting nonazeotropic ether/hydrocarbon mixture can be separated by simple distillation.

The process for producing an alkyl tert-alkyl ether comprises (a) reacting an olefin having a double bond at a tertiary carbon atom and a primary alcohol in the presence of a catalyst under conditions sufficient to effect a condensation reaction whereby an alcohol/ether/hydrocarbon product mixture is produced;

(b) introducing the alcohol/ether/hydrocarbon product mixture into a plurality of adsorption columns operated in cycle in a predetermined timed sequence, each adsorption column containing an adsorbent wherein the following sequence of operational steps is performed in the order recited in each of the adsorption columns in its turn:

(1) passing the alcohol/ether/hydrocarbon product mixture through an adsorption column containing the solid adsorbent and selectively adsorbing the alcohol while discharging an enriched ether/hydrocarbon stream;

(2) rinsing the adsorption column in a direction co-current to the direction of feed flow of step (1) with the alcohol whereby residual ether/hydrocarbon admixture is displaced from the adsorption column and withdrawing an alcohol/ether/hydrocarbon admixture from the adsorption column; and (3) rinsing the adsorption column with a liquid hydrocarbon desorbent and withdrawing an alcohol/desorbent admixture from the adsorption column;

(c) recycling the alcohol/hydrocarbon admixture from step (b:3) to be reacted with additional olefin; and (d) separating the enriched ether/hydrocarbon stream from step (b:1) by distillation to produce a hydrocarbon product and a high purity alkyl tert-ether product.

The process according to the present invention is distinguished from prior art processes in that the cyclic adsorption step for breaking the azeotropic alcohol/ether/hydrocarbon product mixture avoids the use of water washing and vapor-phase desorption/stripping steps in favor of a more energy efficient cyclic liquid-phase adsorption-desorption sequence.

BRIEF DESCRIPTION OF THE DRAWINGS

The sole FIGURE is a process flow diagram of an embodiment according to the present invention.

DETAILED DESCRIPTION OF THE INVENTION

The present invention provides an energy efficient, cyclic process for effectively breaking the alcohol/ether/hydrocarbon azeotrope which is formed during the production of various ethers. Representative of such ethers are the alkyl-tert alkyl ethers, methyl-tert-butyl ether (MTBE), ethyl-tert butyl ether (ETBE) and tert-amyl methyl ether (TAME), which enjoy considerable commercial success as motor fuel octane enhancers. Considerable capital costs and energy are required to break the azeotropic product into its respective components. The instant process overcomes such shortcomings by employing a novel cyclic adsorption sequence to break the azeotropic mixture. More particularly, the alcohol is selectively adsorbed from the azeotropic alcohol/ether/hydrocarbon feedstock mixture whereby the resulting non-azeotropic ether/hydrocarbon mixture can be easily separated by distillation to provide the corresponding alkyl tert-alkyl ether and hydrocarbon products.

The process utilizes a unique concentration swing adsorption sequence for the removal of alcohol from the azeotropic mixture which represents an advance over other continuous, cyclic adsorption processes known in the art. The cyclic adsorption sequence disclosed herein is referred to as a concentration swing adsorption process because the adsorption and desorption steps are governed by changes in concentration of the liquid adsorbates inside the adsorption column containing the adsorbent which selectively adsorb the alcohol component of the azeotropic mixture to provide an ether/hydrocarbon stream which can be easily separated by distillation.

The process for producing an alkyl tert-alkyl ether comprises (a) reacting an olefin having a double bond at a tertiary carbon atom and a primary alcohol in the presence of a catalyst under conditions sufficient to effect a condensation reaction whereby an alcohol/ether/hydrocarbon product mixture is produced;

(b) introducing the alcohol/ether/hydrocarbon product mixture into a plurality of adsorption columns operated in cycle in a predetermined timed sequence, each adsorption column containing an adsorbent wherein the following sequence of operational steps is performed in the order recited in each of the adsorption columns in its turn:

(1) passing the alcohol/ether/hydrocarbon reaction product mixture through an adsorption column containing the solid adsorbent and selectively adsorbing the alcohol while discharging an enriched ether/hydrocarbon stream;

(2) rinsing the adsorption column in a direction co-current to the direction of feed flow of step (1) with the alcohol whereby residual ether/hydrocarbon is displaced from the adsorption column and withdrawing a stream comprising an alcohol/ether/hydrocarbon admixture from the adsorption column; and (3) rinsing the adsorption column with a liquid hydrocarbon desorbent and withdrawing an alcohol/hydrocarbon admixture from the adsorption column;

(c) recycling the methanol/hydrocarbon admixture from step (b:3) to be reacted with additional olefin feed; and (d) separating the enriched ether/hydrocarbon stream from step (b:1) by distillation to produce a hydrocarbon product and a high purity alkyl tert-ether product.

The invention will be described in greater detail with reference to the sole FIGURE which illustrates a schematic diagram of an apparatus for producing alkyl-tert-alkyl ethers. The schematic consists of ether reactor 14, three parallel adsorption columns 1 through 3., numerous control valves; liquid manifolds A through F; liquid pumps 18, 57 and 62., storage tanks 52 and 64 and distillation column 68.

The first step of the process comprises reacting an olefin having a double bond on a tertiary carbon atom and a primary alcohol in the presence of a catalyst under conditions sufficient to effect a condensation reaction whereby an alcohol/ether/hydrocarbon mixture is produced. A combined alcohol and alkene feed stream 10 is mixed with alcohol recycle stream 11 and passed through line 12 into alkyl-tert-alkyl ether reactor 14. The alcohol and alkene reactant mixture is contacted with a catalyst under conditions sufficient to form the corresponding alkyl-tert-alkyl ether. The ether product, along with unreacted alcohol, which is typically added in excess, and hydrocarbon, is withdrawn from reactor 14 and passed through line 16, with the aid of pump 18, Manifold A and into the cyclic adsorption system wherein the respective components of the azeotropic reaction product mixture are separated into an alcohol fraction and a nonazeotropic ether/hydrocarbon fraction.

The etherification reaction may be carried out under any suitable reaction conditions known in the art. For example, in the production of MTBE, the mole ratio of methanol to isobutylene usually ranges from about 0.05 to about 10, and preferably from about 1 to about 10. The reaction temperature may vary from about 60° F. to about 300° F., but more usually the reaction is carried out at a temperature ranging from about 120° F. to about 200° F. The pressure employed is that pressure sufficient to maintain the reactants in the liquid phase and typically ranges from about 30 psig to about 300 psig.

The reactants are contacted in the presence of an acid-type ion-exchange resin such as a high molecular weight carbonaceous material containing sulfonate groups. Sulfonated resins of various types are widely available under various commercial names and of various types such as the sulfonated coals, phenol formaldehyde resins reactive with sulfuric acid, sulfonated resinous polymers of cumerone-indene with cyclopentadiene, various commercially available strongly acidic cationic exchange resins such as sulfonated polystyrene resins and others. The catalyst is typically employed in a finely divided state having a mesh size of about 10 to 50 US sieve. Preferably, a fixed bed of particulate solid ion-exchange resin catalyst is utilized to carry out the reaction.

The next step in the process comprises breaking the azeotropic product mixture into its respective components wherein a cyclic concentration swing adsorption process is utilized to selectively adsorb the alcohol from the alcohol/ether/hydrocarbon product mixture. The concentration swing adsorption process comprises a single adsorption column or a plurality of adsorption columns containing an adsorbent selective toward the retention of the alcohol wherein the adsorption cycle is operated in cycle in a predetermined sequence. Each adsorption column undergoes a sequence of operational steps performed in the order recited herein.

According to the FIGURE, Manifold A is placed in flow communication with branch inlet lines 21, 31 and 41 which are connected to the inlet ends of adsorption columns 1, 2 and 3, respectively. Lines 21, 31 and 41 are equipped with valves 21a, 31a and 41a, respectively. Opening of the appropriate valve permits flow of the ether/alcohol/hydrocarbon azeotropic product mixture from reactor 14 into the selected adsorption column being placed on stream. Thus, by opening valve 21a, while valves 31a, and 41a are closed, the product azeotropic mixture is caused to flow from reactor 14, through lines 16 and 21, as assisted by pump 18, and into adsorption column 1.

Adsorption columns 1, 2 and 3 are fitted at their respective outlet ends with lines 22, 32 and 42, respectively, each further equipped with control valves 22a, 32a and 42a, respectively. Lines 22, 32 and 42 are operatively connected to manifold F through which the nonazeotropic ether/hydrocarbon stream flows into distillation column 68 wherein the mixture is separated into an overhead hydrocarbon product which flows through line 72 and into an optional hydrocarbon storage tank (not shown) and an ether bottoms product which flows through line 70 into an optional ether storage tank (not shown).

Adsorption columns 1, 2 and 3 are operatively connected to lines 23, 33 and 43, each being further provided with control valves 23a, 33a and 43a, respectively, such lines being placed in flow communication with manifold B. Manifold B is in flow communication with alcohol/hydrocarbon storage tank 52. By opening the appropriate control valve 23a, 33a or 43a, an alcohol/hydrocarbon mixture from storage tank 52 is caused to flow through line 50 into a desired adsorption column.

Each adsorption column is placed in flow communication with discharge manifold C via lines 24, 34, 44 and 54, each of which is equipped with control valves 24a, 34a, 44a and 54a. By opening the appropriate valve 24a, 34a, 44a or 54a pure alcohol from an alcohol storage tank (not shown), or alternatively, from line 54, is caused to be pumped via pump 57 through manifold C and into the appropriate adsorption column.

Adsorption columns 1, 2 and 3 are placed in flow communication with manifold D via lines 25, 35 and 45, which are fitted with control valves 25a, 35a and 45a, respectively. By opening the appropriate control valve, the column effluent is caused to flow through manifold D and line 17 for admixture with the alcohol/ether/hydrocarbon product mixture produced in reactor 14. The discharge ends of columns 1, 2 and 3 are operatively connected to manifold E via lines 26, 36 and 46, each which are fitted with control valves 26a, 36a and 46a, respectively. By opening the appropriate valve 26a, 36a or 46a, effluent from a particular adsorption column is caused to enter lines 22, 32 or 42 flowing into lines 26, 36, or 46 and into manifold E. Manifold E is operatively connected to hydrocarbon storage container 64 via line 63. Hydrocarbon storage container 64 is placed in flow communication with manifold F via line 65 and control valve 65a.

Adsorption columns 1, 2 and 3 are operatively connected to manifold F via lines 22, 32, 42 which are further equipped with control valves 22a, 32a and 42a, respectively. By opening the appropriate control valve 22a, 32a or 42a, ether/hydrocarbon mixture is caused to flow from the discharge end of the respective adsorption column and into distillation column 68 for separation into pure hydrocarbon and ether products.

Operation of the embodiment represented in the sole FIGURE will now be explained in connection with an arbitrarily chosen cycle having three timed separation periods of sixty minutes per period as set forth in Table 1. Although not limited thereto, the process as illustrated in the sole FIGURE requires 3 adsorption columns for continuous operation. However, other arrangements using a greater or lesser number of adsorption columns may be employed if interrupted or discontinuous operation (using idling) of pumps is acceptable. Similarly, the total cycle time of 180 minutes is chosen as an example. Other total cycle times varying between three minutes to nine hours can be selected depending on the size of the plant.

The cyclic concentration swing adsorption scheme will now be explained in greater detail. Each of the three respective adsorption columns 1 through 3 undergoes one period of the adsorption step, one period of the alcohol rinse step and one period of the desorbent-rinse step. As illustrated in Table 1, the steps undertaken at startup in each of the respective adsorption columns 1 through 3 are staggered to enable at least one of the three adsorption columns to undergo the adsorption step at all times during the process cycle.

TABLE 1

| Time (min.) | Column 1 | Column 2 | Column 3 |
|---|---|---|---|
| 0–60 | Adsorption | Desorbent Rinse | Alcohol Rinse |
| 60–120 | Alcohol Rinse | Adsorption | Desorbent Rinse |
| 120–180 | Desorbent Rinse | Alcohol Rinse | Adsorption |

The operation of the invention illustrated in the sole FIGURE involves principally the following sequence of steps:

(a). Adsorption—a feed stream of the azeotropic alcohol/ether/hydrocarbon mixture is passed through an adsorption column containing adsorbent preferentially selective toward retention of the alcohol wherein a substantially alcohol-free ether/hydrocarbon stream is withdrawn from the discharge end of the adsorption column. The alcohol is selectively adsorbed onto the adsorbent and a mass transfer zone (MTZ) is formed inside the adsorbent which moves toward the outlet or discharge end of the column as more azeotropic product mixture is passed. The liquid composition at the leading edge of the mass transfer zone is enriched in the ether/hydrocarbon mixture while the liquid composition at the trailing edge of the MTZ has a feed-like composition. The adsorption step is continued until the MTZ reaches the effluent end of the column or somewhat short of it. The column effluent, which is a nonazeotropic mixture of ether and hydrocarbon, is subsequently transferred to distillation column 68 for separation into a pure, substantially alcohol-free ether bottom product which is withdrawn from line 70 and a hydrocarbon stream which is withdrawn as an overhead product from line 72. The hydrocarbon stream can be recycled as described herein.

(b). Alcohol Rinse—the adsorption column is rinsed with essentially pure alcohol in a direction co-current to the direction of the feedstock flow. The adsorption column effluent for this step is mixed with the fresh ether reactor effluent and transferred to the cyclic adsorption process system as feed stock. The alcohol-rinse step is continued until the adsorption column is essentially saturated with the alcohol.

(c). Desorbent-Rinse—the adsorption column is rinsed with a desorbent liquid, which can be a fresh $C_4$–$C_5$ hydrocarbon stream, in a direction countercurrent to the feedstream to desorb and remove void alcohol from the adsorption column. Initially, the column effluent contains a relatively pure alcohol stream which can be used in the alcohol rinse step. The effluent stream in the latter part of this step contains a mixture of alcohol and $C_4$–$C_5$ hydrocarbon which can be utilized as additional ether reactor feedstock. As will be discussed herein, the source of the hydrocarbon rinse liquid can be supplied from fresh feed (line 60) or from the stock of hydrocarbon storage tank 64. In a preferred embodiment, the desorbent rinse step is effected by utilizing fresh hydrocarbon for a portion of the step cycle time followed by a rinse using $C_4$ hydrocarbon stored in hydrocarbon storage tank 64 for the remaining time of the period.

The valve positions during the above-mentioned operating cycle are set forth in Table 2. The designation O indicates that the valve is open while a C represents a closed valve. The operative sequence of steps occurring in adsorption column 1 during a complete adsorption cycle will now be described in exhaustive detail so that operation of a continuous process will be fully understood. The identical sequence of steps according to Table 1 occurs in staggered sequence in adsorption columns 2 and 3.

Again, referring to the embodiment disclosed in the FIGURE and the sequence periods and valve positions designated in Tables 1 and 2, adsorption column 1 undergoes one sequence period of the adsorption step. The azeotropic alcohol/ether/hydrocarbon product stream from reactor 14 is introduced into adsorption column 1 by opening valves 21a and 22a and closing valves 31a and 41a thereby allowing feedstock from reactor 14 to flow through line 16, manifold A, line 21, as assisted by pump 18, and into adsorption column 1 which contains an adsorbent which is preferentially selective toward adsorption of alcohol. The adsorption step is continued until the adsorbent in adsorption column 1 is essentially saturated with the feed mixture.

Alcohol is selectively adsorbed onto the adsorbent and a mass transfer zone (MTZ) is formed within the adsorption column which moves toward the discharge end of adsorption column 1 as more feedstock is passed through the column. The adsorption step is completed when the MTZ reaches the effluent or discharge end of the adsorption column or somewhat short of it by a predesigned set point.

TABLE 2

| | Valve Operation Schedule | | |
|---|---|---|---|
| Valve | Adsorption 0–t1 | Rinse t1–t2 | Desorotion t2–t3 |
| 21a | O | C | C |
| 22a | C | C | C |
| 23a | C | C | O |
| 24a | C | O | C |
| 25a | O | O | C |
| 26a | C | C | O |
| 31a | C | C | C |
| 32a | C | C | C |
| 33a | C | C | C |
| 34a | C | C | C |
| 35a | C | C | C |
| 36a | C | C | C |
| 41a | C | C | C |
| 42a | C | C | C |
| 43a | C | C | C |
| 44a | C | C | C |
| 45a | C | C | C |
| 46a | C | C | C |
| 54a | C | O | C |
| 60a | C | C | O |
| 65a | C | C | C |

The less selectively adsorbed components, namely, the ether/hydrocarbon mixture, exit the discharge end of column 1 via line 22 and flows through manifold F into distillation column 68 wherein the ether/hydrocarbon mixture is separated into an overhead hydrocarbon stream 72 and a bottom ether product which exits distillation column 68 via line 70.

At the end of the adsorption step, Column 1 is rinsed with a fresh alcohol stream in order to displace void liquids within the adsorption column. More particularly, valves 24a and 25a are opened enabling alcohol from stream 56, or alternatively, alcohol from recycle stream 54, to be pumped via pump 57 through manifold C and lines 24 and 22 into column 1 in a direction co-current to the feedstock. The adsorption column effluent during this step is passed through line 25, manifold D and line 17 to be mixed with reactor product effluent from stream 16. This step is continued until the adsorbent in adsorption column 1 is essentially saturated with alcohol.

The final step in the concentration swing adsorption sequence involves rinsing the adsorbent residing in adsorption column 1 with a fresh hydrocarbon desorbent stream. Control valves 23a and 26a are opened and fresh reactor feed hydrocarbon from a hydrocarbon storage tank (not shown) is pumped via pump 62 through lines 60 and 63, manifold E and lines 26 and 22 into column 1 in a direction counter-current to the flow of the adsorption feedstock. Initially, the column effluent contains a relatively pure alcohol stream which can be utilized in the alcohol-rinse disclosed above. More particularly, the alcohol-rich stream flows through line 21, line 23, manifold B and line 50 wherein the alcohol fraction can be transferred into manifold C by opening valve 54a.

The later fractions of column effluent contain a mixture of alcohol and C4 hydrocarbon which is routed to alcohol/hydrocarbon storage tank 52 by closing valve 54a. This step is continued until adsorption column 1 is essentially saturated with the desorbent hydrocarbon. Optionally, the alcohol/hydrocarbon mixture can be separated by distillation to recover an alcohol fraction and a hydrocarbon fraction. If this option is practiced, a distillation column (not shown) will be required to process a portion of the column effluent. In a preferred embodiment, the desorption sequence period is split into two subperiods wherein the source of the hydrocarbon desorbent during the first subperiod is fresh reactor feed hydrocarbon (line 60) and the source of desorbent during the second subperiod is hydrocarbon storage tank 64.

While the relative length of each of the above-mentioned subperiods may vary, the first subperiod is typically substantially longer than the second subperiod. Assuming a 60 minute sequence time for each desorption step, the first subperiod may be 58 minutes and the second subperiod may be 2 minutes in duration. Those skilled in the art will understand that the flow direction of the hydrocarbon desorbent stream into the adsorption column may be either cocurrent or countercurrent to the feedstock flow. Column 1 is essentially saturated with the hydrocarbon desorbent at the end of this step and the column is prepared to start another process cycle beginning with the adsorption step.

The selective adsorption step of the process proceeds according to the above-mentioned steps enumerated in Table 1. While the sequence periods are depicted as being of equal length, this is neither required or necessary. The times will be set by allowable maximum liquid flow rates, valve and line sizes and the properties of the adsorbent used. Alternate routines may be employed for establishing the duration of each of the cycle steps. For example, the end of a particular step may be determined by other techniques known in the art such as by analysis of the composition of the adsorption column effluent.

The process described in each of the embodiments of this invention is preferably run utilizing adsorbents having a relatively small particle diameter of about 0.2 to about 0.8 mm although a broad range of particle sizes can be employed. This preferred particle size will shorten the distance of diffusion of the adsorbate molecules and will enhance the rate of adsorption. On the other hand, smaller particles will increase the pressure drop within the column during all steps of the process cycle. This pressure drop is overcome by compressing the liquid streams entering the adsorbent within each adsorption column to a pressure of about 10 to 150 psig. Since liquids are incompressible fluids, such compression will not significantly add to the energy requirements of the separation process.

The primary alcohols suitable for practicing the present invention are those alcohols having from 1 to about 8 carbon atoms and include methanol, ethanol, propanol, butanol and pentanol. Olefins suitable for practicing the present invention are those olefins having a double bond of a tertiary carbon atom which possess from 2 to about 10 carbon atoms. Preferred olefins include isobutylene and the isopentenes. The process according to the present invention is particularly suited for the production of methyl tert-butyl ether, wherein methanol is reacted with isobutylene, ethyl tert-butyl ether, wherein ethanol is reacted with unsaturated $C_4$-$C_5$ hydrocarbons, and tert-amyl methyl ether, wherein methanol is reacted with isopentene. The term isopentene includes all isomers of the five carbon olefin which possess a double bond linked to a tertiary carbon atom.

The following examples are provided to further illustrate various embodiments of the invention for the case of MTBE production and are not intended to restrict the scope of the invention.

EXAMPLE 1

Operation of a Three Bed Cyclic Adsorption MTBE Unit

This example illustrates the design and operation of a simulated plant according to the sole FIGURE. The plant consists of three adsorption columns of 3' diameter and 30' length, each containing a total of 26,000 lbs of 0.5 mm bead 4A zeolite. A conventional etherification reactor known in the art was utilized wherein the reactor was designed to operate at a production rate of 1830 BPSD MTBE at 96% conversion. A 1.05/1 molar ratio of methanol to isobutene was utilized in preparing the ether. The feed temperature of azeotropic ether/alcohol/hydrocarbon into the adsorption column was about 30° C. The three bed cyclic adsorption unit was operated utilizing a 180 minute cycle as enumerated in Table 3. The relative composition of the MTBE reactor feed (stream 14) and the MTBE reactor effluent (stream 17) is also provided in Table 3. Table 3 demonstrates that the conversion from isobutene to MTBE is about 96% wherein the MTBE product is approximately 97% pure. Table 4 presents a description of various process streams according to the sole FIGURE.

TABLE 3

| Reactor Feed and Product Composition | | |
|---|---|---|
| Composition (wt %) | C4 Feed | Reactor Effluent |
| Isobutane | 27.4 | 24.1 |

TABLE 3-continued

| Reactor Feed and Product Composition | | |
|---|---|---|
| Composition (wt %) | C$_4$ Feed | Reactor Effluent |
| N-Butane | 9.1 | 8.0 |
| Isobutane | 14.1 | 0.4 |
| 1-Butene | 12.6 | 12.1 |
| Trans 2-Butene | 16.2 | 15.1 |
| Cis 2-Butene | 12.2 | 12.1 |
| Isopentane | 3.2 | 3.0 |
| Methanol | — | — |
| MTBE | — | — |
| Others | 5.2 | 4.5 |
| | 100 | 100 |

TABLE 4

| Adsorption Cycle and Process Stream Description | |
|---|---|
| Cycle Time: | |
| Adsorption: | 60 minutes |
| Methanol Rinse | 60 minutes |
| Fresh Hydrocarbon Reactor Feed Rinse (stream 60) | 58 minutes |
| Product Hydrocarbon Rinse | 2 minutes |

| Stream No. | Stream Description | lb-Mole/Cycle |
|---|---|---|
| 18 | Feed to Adsorption column | 1557 |
| 16 | Reactor Effluent | 1523 |
| 24 | Recycle from MeOH Rinse | 34 |
| 26 | Effluent During Adsorption | 1553 |
| 44 | Methanol Rinse | 120 |
| 34 | Fresh Hydrocarbon Reactor Feed Rinse | 1482 |
| 36 | Product Hydrocarbon Rinse | 48 |

The process according to the present invention offers significant advantages over prior art processes. In contrast to French Patent 2,448,521-A which utilizes a vapor phase desorption step requiring considerable energy output to vaporize and condense the desorbent and product streams, the present invention offers a continuous, liquid phase process which utilizes a cyclic adsorption scheme which is operated in the liquid phase. Moreover, the present invention requires substantially less equipment to operate and can be operated with substantially lower energy requirements while offering a very high recovery of the ether product (99%+) at high purity 99%+).

Having thus described the present invention, what is now deemed appropriate for Letters Patent is set forth in the following appended claims.

We claim:

1. A process for producing an alkyl tert-alkyl ether comprising:
   (a) reacting an olefin having a double bond at a tertiary carbon atom and a primary alcohol in the presence of a catalyst under conditions sufficient to effect a condensation reaction whereby a mixture of the alkyl tert-alkyl ether, unreacted alcohol and unreacted olefin is produced;
   (b) introducing the mixture into a first column of a plurality of adsorption columns containing an adsorbent each of the plurality of adsorption columns which undergoes the sequential steps of:
      (1) passing the mixture through the first adsorption column containing the adsorbent and selectively adsorbing the unreacted primary alcohol while discharging a stream comprising a mixture of the alkyl tert-alkyl ether and the unreacted olefin;
      (2) rinsing the adsorption column in a direction co-current to the direction of feed flow of step (1) with the primary alcohol whereby a mixture of residual alkyl tert-alkyl ether and unreacted olefin is displaced and withdrawn from the adsorption column; and
      (3) rinsing the adsorption column with the olefin and withdrawing a mixture of unreacted primary alcohol and unreacted olefin from the adsorption column;
   (c) recycling mixture of unreacted primary alcohol and unreacted olefin from step (b:3) by combining the mixture with the feedstream recited in step (a); and
   (d) separating the stream from step (b:1) by distillation to produce unreacted olefin product and the alkyl tert-ether.

2. The process according to claim 1 wherein the alcohol is selected from primary alcohols having from 1 to about 8 carbon atoms.

3. The process according to claim 2 wherein the primary alcohol is selected from methanol, ethanol, propanol, butanol and pentanol.

4. The process according to claim 1 wherein the olefin has from 4 to about 10 carbon atoms.

5. The process according to claim 4 wherein the olefin is selected from isobutylene and isopentene.

6. The process according to claim 1 wherein the liquid desorbent is a C$_4$ to C$_5$ olefin.

7. The process according to claim 1 wherein the alcohol is methanol and the olefin is isopentene.

8. The process according to claim 1 wherein the alcohol is ethanol and the olefin is isobutylene.

9. The process according to claim 1 wherein the adsorbent is a 4A zeolite.

10. The process according to claim 1 wherein the adsorber feedstock is compressed to a pressure ranging from about 10 to 150 psig.

11. A process for producing methyl tert-butyl ether comprising:
   (a) reacting a feedstream comprising isobutene and methanol in the presence of a catalyst under conditions sufficient to effect a condensation reaction whereby a mixture of the methyl tert-butyl ether, unreacted isobutene and unreacted methanol is produced;
   (b) introducing the mixture into a first column of a plurality of adsorption columns containing 4A zeolite adsorbent, each of the plurality of adsorption columns which undergoes the sequential steps of:
      (1) passing the mixture through the first adsorption column containing the 4A zeolite adsorbent and selectively adsorbing the unreacted methanol while discharging an enriched steam comprising a mixture of the methyl tert-butyl ether and the unreacted isobutene;
      (2) rinsing the adsorption column with methanol in a direction co-current to the direction of feed flow of step (b) (1) whereby a mixture of residual methyl tert-butyl ether and unreacted isobutene is displaced and withdrawn from the adsorption column; and
      (3) rinsing the adsorption column with isobutene and withdrawing a mixture of unreacted methanol and unreacted isobutene from the adsorption column;
   (c) recycling the mixture of unreacted methanol and unreacted isobutene recited in step (b:3) by combining the mixture with the feedstream recited in step (a); and
   (d) separating the enriched stream of step (b:1) comprising the mixture of methyl tert-butyl ether and unreacted isobutene by distillation to produce an isobutene product and the alkyl tert-ether.

* * * * *